US 11,464,929 B2

(12) United States Patent
Peesay et al.

(10) Patent No.: US 11,464,929 B2
(45) Date of Patent: Oct. 11, 2022

(54) SYSTEM AND METHOD FOR VIBRATORY, HIGH FREQUENCY VENTILATION OF NEONATES AND INFANTS

(71) Applicant: Georgetown University, Washington, DC (US)

(72) Inventors: Morarji Peesay, Columbia, MD (US); Kabir Abubakar, Columbia, MD (US)

(73) Assignee: Georgetown University, Washington, DC (US)

(*) Notice: Subject to any disclaimer, the term of this patent is extended or adjusted under 35 U.S.C. 154(b) by 558 days.

(21) Appl. No.: 15/275,526

(22) Filed: Sep. 26, 2016

(65) Prior Publication Data

US 2017/0087317 A1 Mar. 30, 2017

Related U.S. Application Data

(60) Provisional application No. 62/232,475, filed on Sep. 25, 2015.

(51) Int. Cl.
*A61M 16/00* (2006.01)
*A61M 16/06* (2006.01)
(Continued)

(52) U.S. Cl.
CPC .... *A61M 16/0096* (2013.01); *A61M 16/0672* (2014.02); *A61M 16/0833* (2014.02);
(Continued)

(58) Field of Classification Search
CPC .......... A61M 16/0096; A61M 16/0672; A61M 16/0677; A61M 16/0666; A61M 16/06; A61M 16/0833; A61M 16/0808; A61M 16/0819; A61M 16/0825; A61M 16/0841; A61M 16/085; A61M 16/0858;
(Continued)

(56) References Cited

U.S. PATENT DOCUMENTS 4,821,709 A * 4/1989 Jensen .............. A61M 16/0096
128/204.21
2003/0189492 A1 10/2003 Harvie
(Continued)

OTHER PUBLICATIONS

De Luca, Daniele, et al. "Noninvasive high frequency oscillatory ventilation through nasal prongs: bench evaluation of efficacy and mechanics." Intensive care medicine 36.12 (2010): 2094-2100.
(Continued)

*Primary Examiner* — Elliot S Ruddie
(74) *Attorney, Agent, or Firm* — Smith Gambrell & Russell LLP

(57) ABSTRACT

One aspect of the present disclosure relates to a system for providing non-invasive, high frequency ventilation to a neonate or an infant in need thereof. The system can include a tubing array, a vibration device, and a bifurcated cannula. The tubing array can be adapted to receive a flow of pressurized gas therethrough. The vibration device can be fluidly coupled to the tubing array and configured to generate and apply a jet of air to the flow of pressurized gas. The bifurcated cannula can be fluidly coupled to the tubing array and have independently movable first and second prongs that are sized and dimensioned for insertion into first and second nostrils, respectively, of the neonate or the infant.

15 Claims, 6 Drawing Sheets

(51) Int. Cl.
*A61M 16/08* (2006.01)
*A61M 16/16* (2006.01)

(52) U.S. Cl.
CPC ......... *A61M 16/0875* (2013.01); *A61M 16/16* (2013.01); *A61M 2016/0042* (2013.01); *A61M 2209/02* (2013.01); *A61M 2230/432* (2013.01); *A61M 2240/00* (2013.01)

(58) Field of Classification Search
CPC .......... A61M 16/0875; A61M 16/0883; A61M 16/0891; A61M 16/16; A61M 2016/0042; A61M 2016/0039; A61M 2016/0033; A61M 2016/003; A61M 2209/02; A61M 2230/432; A61M 2240/00
USPC ........................................ 128/204.18, 204.21
See application file for complete search history.

(56) References Cited

U.S. PATENT DOCUMENTS

| 2007/0125387 A1* | 6/2007 | Zollinger ........... A61M 16/0611 128/207.18 |
| 2013/0186399 A1 | 7/2013 | Gutmark et al. |

OTHER PUBLICATIONS

Mukerji, Amit, et al. "Use of noninvasive high-frequency ventilation in the neonatal intensive care unit: a retrospective review." American journal of perinatology 32.02 (2015): 171-176.

Yoder, Bradley A., Kurt H. Albertine, and D. M. Null. "High-frequency ventilation for non-invasive respiratory support of neonates." Seminars in Fetal and Neonatal Medicine. vol. 21. No. 3. WB Saunders, 2016.

* cited by examiner

SYSTEM AND METHOD FOR VIBRATORY, HIGH FREQUENCY VENTILATION OF NEONATES AND INFANTS

RELATED APPLICATION

This application claims the benefit of U.S. Provisional Patent Application Ser. No. 62/232,475, filed Sep. 25, 2015, the entirety of which is hereby incorporated by reference for all purposes.

TECHNICAL FIELD

The present disclosure relates generally to systems and methods for ventilating neonates and infants and, more particularly, to a system and method for delivering vibratory, high frequency ventilation of neonates and infants.

BACKGROUND

As a result of respiratory failure, it occasionally becomes difficult for particular individuals to breathe without assistance of a respirator or other mechanical apparatus, which tends to achieve adequate gas exchange between the blood/lungs and the atmosphere.

A variety of respirators are used to ventilate patients mechanically. Conventional ventilators are operated on a rate of 1-120 cycles/minute (breaths per minute). Such conventional respirators often cause trauma to the airways and to the lungs due to high volume and pressure delivered, and may often fail to provide adequate gas exchange.

To try and solve this problem, methods for high-frequency ventilation have been developed, which use less than physiologic tidal volumes in conjunction with high respiratory rates of 2-30 Hz (120-1,800 rounds or cycles per minute). Several methods and devices for the delivery of high-frequency ventilation have been patented and some of them are used clinically for the ventilation of patients, but with limited success.

SUMMARY

The present disclosure relates generally to systems and methods for ventilating neonates and infants and, more particularly, to a system and method for delivering vibratory, high frequency ventilation of neonates and infants.

One aspect of the present disclosure relates to a system for providing high frequency ventilation to a neonate or an infant in need thereof. The system can include a tubing array, a vibration device, and a bifurcated cannula. The tubing array can be adapted to receive a flow of pressurized gas therethrough. The vibration device can be fluidly coupled to the tubing array and configured to generate and apply a jet of air to the flow of pressurized gas. The bifurcated cannula can be fluidly coupled to the tubing array and have independently movable first and second prongs that are sized and dimensioned for insertion into first and second nostrils, respectively, of the neonate or the infant.

Another aspect of the present disclosure relates to a method for providing high frequency ventilation to a neonate or infant in need thereof. One step of the method can include generating a jet of high frequency oscillatory air. The jet of high frequency oscillatory air can be generated by oscillatory motion of one or more vibrating elements within a housing of a vibration device. The vibration device can be fluidly coupled to a tubing array adapted to receive a flow of pressurized gas therethrough. The jet of high frequency oscillatory air can be directed through a first prong and/or a second prong of a bifurcated cannula, which is fluidly coupled to the tubing array and positioned proximate to the first and/or second nostril(s) of the neonate or the infant, respectively.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
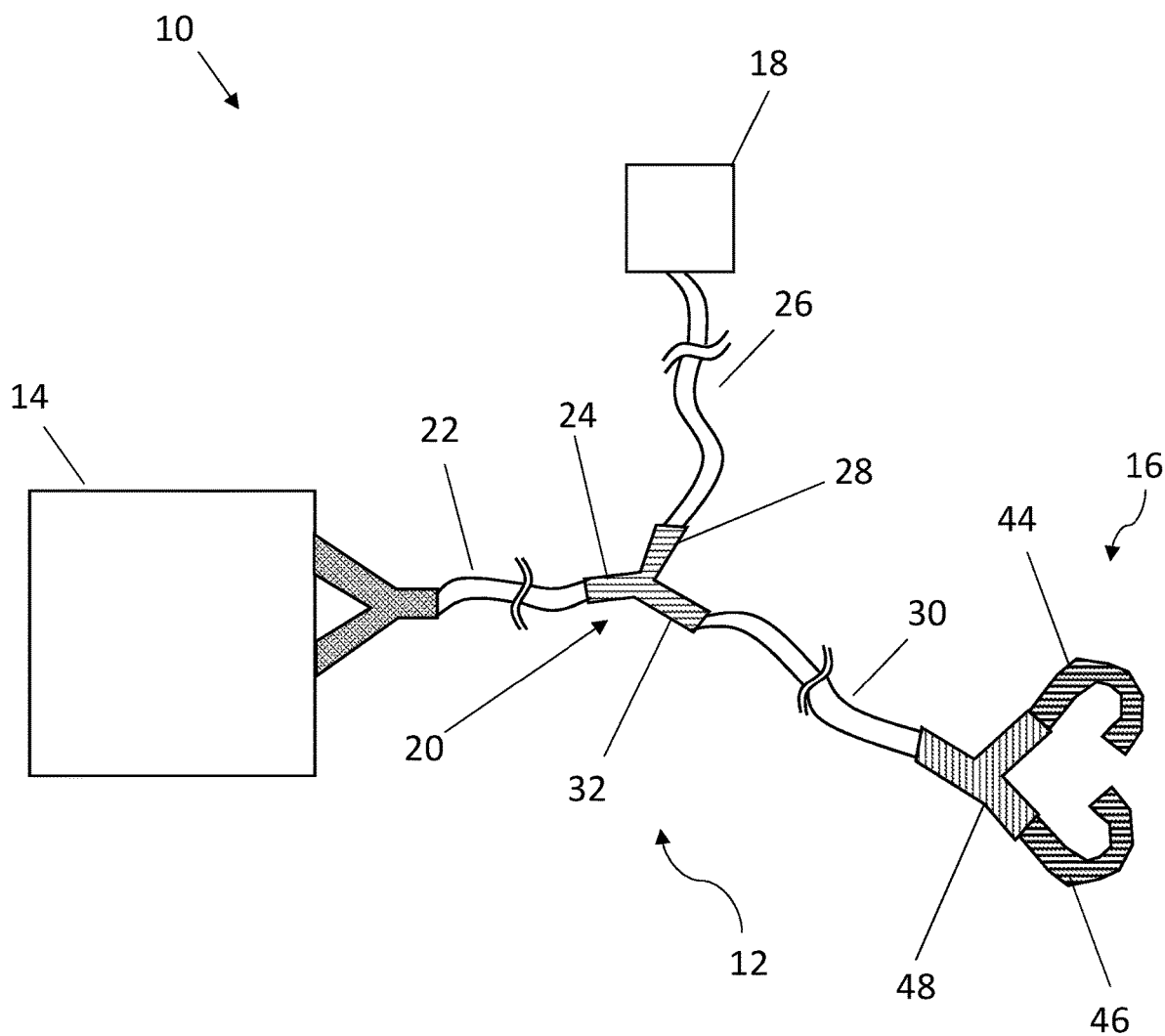
FIG. 1 is a schematic illustration showing a system for providing high frequency ventilation to a neonate or an infant in need thereof constructed in accordance with one aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "fluidly coupled" can be used interchangeably with "fluid communication" and refer to a path or route through which a fluid (e.g., water or a gas) may flow between two components, either directly or through one or more intermediate components. In other words, fluid communication between two components can mean that a fluid can flow from one component to another but does not exclude one or more intermediate components between the two recited components which are in fluid communication. Thus, a fluid inlet and outlet can be in "fluid communication" with one another, even though there are one or more conduits extending therebetween as well as one or more valves which serve to regulate the flow of fluid between the inlet and outlet.

As used herein, the term "electrical communication" can be used interchangeably with "electrically coupled" and can refer to a path or route through which an electrical current (e.g., a signal) may flow between two components, either directly or through one or more intermediate components. Such a path or route may be direct (e.g., a wire or other electrically-conductive structure) or indirect (e.g., wireless).

As used herein, the term "neonate" can refer to an infant less than thirty days old (e.g., less than one day old).

As used herein, the term "non-invasive" can refer to pulmonary or breathing therapy associated with the present disclosure that does not require patient intubation.

As used herein, the term "infant" can refer to a subject not more than about one year of age, and includes infants from 0 to about 4 months of age, infants from about 4 to about 8 months of age, infants from about 8 to about 12 months of age, low birth weight infants at less than 2,500 grams at birth, and preterm infants born at less than about 37 weeks gestational age, typically from about 26 weeks to about 34 weeks gestational age.

Overview

The present disclosure relates generally to systems and methods for ventilating neonates and infants and, more particularly, to a system and method for delivering vibratory, high frequency ventilation of neonates and infants. The well established high frequency ventilators (HFV) employed in current clinical practice use very high respiratory rates (>150/mt (Vf) breaths per minute) and very small tidal volumes. HFV is thought to reduce ventilator-associated lung injury (VALI). This is commonly referred to as lung protective ventilation. There are different types of HFV. Each type has its own unique advantages and disadvantages. The types of HFV are characterized by the delivery system and the type of exhalation phase. HFV may be used alone or in combination with mechanical ventilation.

It has been shown that there are problems, such as lung damage associated with using high pressure and high volumes to ventilate infants/newborns (and especially preterm infants). Gentle ventilation minimizes damage to vulnerable lungs of these premature patients. Advantageously, the present disclosure utilizes the concept of high frequency respiratory rates that are used in high frequency ventilators to provide non-invasive, HFV to a neonate or infant. As discussed in more detail below, this is achieved by using an electrically-operated vibrating device to vibrate a portion of nasal cannula tubing having continuous gas (e.g., air or oxygen) flow therethrough such that gas flow through the nasal cannula tubing vibrates while being passed through the tubing into the patient—but without intubating the patient. This, in turn, provides vibratory HFV to the neonate or infant without causing lung damage (e.g., VALI) typically associated with such ventilation.

Systems

One aspect of the present disclosure can include a system 10 (FIG. 1) for providing non-invasive, HFV to a neonate or an infant in need thereof, such as pre-term infant or a pre-term neonate. As shown in FIG. 1, the system 10 can comprise a tubing array 12, a vibration device 14 fluidly coupled to the tubing array, and a bifurcated cannula 16 also fluidly coupled to the tubing array.

In another aspect, the tubing array 12 can be adapted to receive a flow of pressurized gas therethrough. The flow of pressurized gas can be generated by a pressurized gas source 18, such as a pressurized canister of oxygen or air. In some instances, the pressurized gas source 18 can be a wall-mounted gas source located, for example, in a surgical suite, a delivery suite, a post-delivery suite, or the like. The tubing array 12 can further include a Y-shaped adaptor 20, a first segment 22 of tubing that fluidly couples the vibration device 14 to a first prong 24 of the Y-shaped adaptor, a second segment 26 of tubing that fluidly couples the pressurized gas source 18 to a second prong 28 of the Y-shaped adaptor, and a third segment 30 of tubing that fluidly couples the bifurcated nasal cannula 16 to a third prong 32 of the Y-shaped adaptor. In one example, all or only a portion of the tubing array 12 can be made of nasal cannula tubing (e.g., single or multi-channel tubing).

Figure 2:
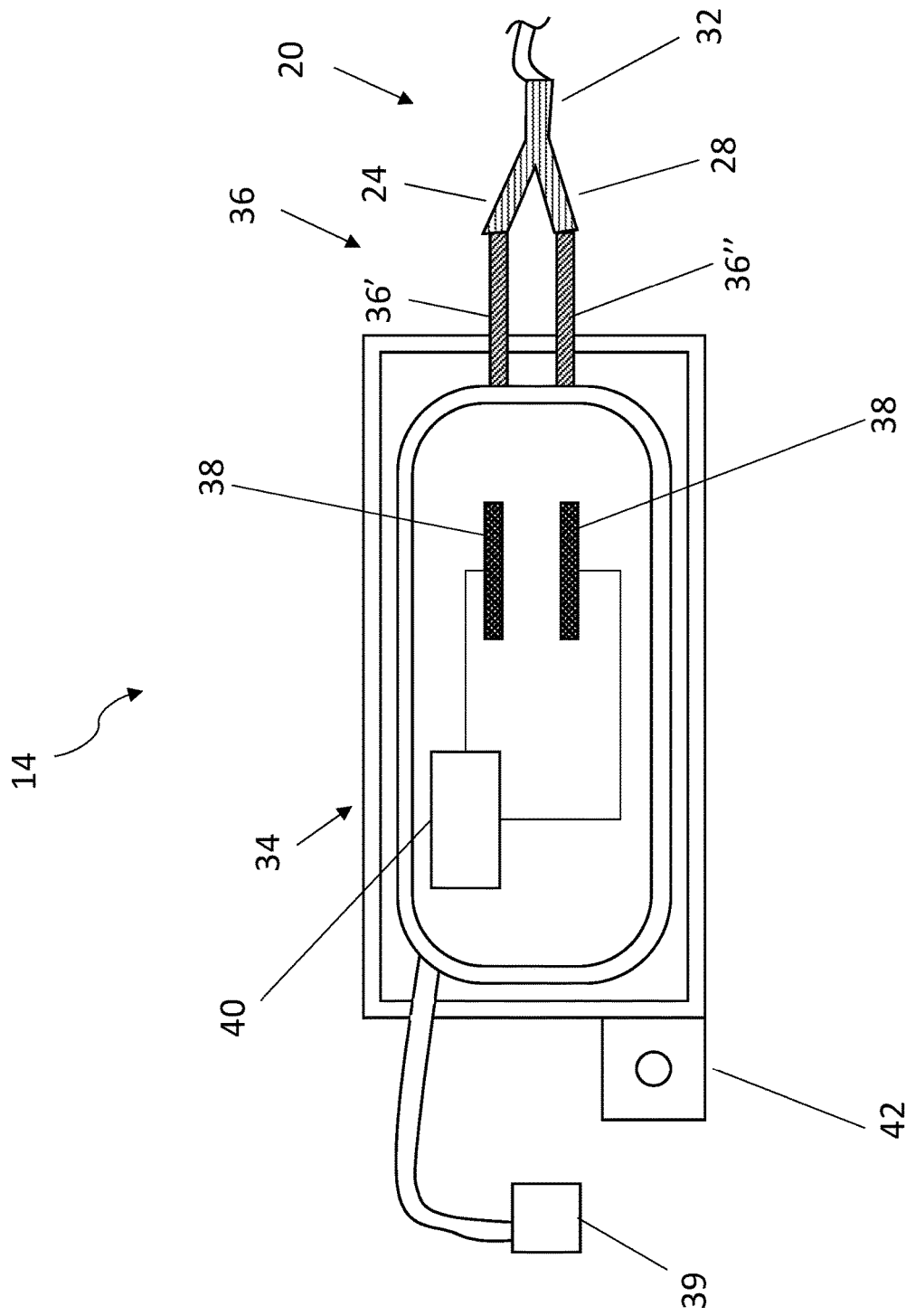
FIG. 2 is a schematic illustration showing a vibration device comprising the system in FIG. 1.

In another aspect, the vibration device 14 can be fluidly coupled to the tubing array 12. The vibration device 14 can be configured or programmed to generate and apply a jet of air to the flow of pressurized gas without the use of an internal or external motor. An exemplary configuration of the vibration device 14 is shown in FIG. 2. In this configuration, the vibration device 14 can comprise a housing 34 having at least one orifice 36, one or more vibrating elements 38 located within the housing, and a signal generator component 40 that is electrically coupled to the one or more vibrating elements. The vibrating elements 38 can be physically spaced apart from each other as shown in FIG. 2. In one example, the vibration device 14 can include two vibrating elements 38, each of which comprises a magnet. The magnets can be physically spaced apart from one another (e.g., such that the magnets are not in direct physical contact with one another). As shown in FIG. 2, for example, the magnets can be located parallel (or substantially parallel) to one another. As discussed below, each of the magnets can have a size and shape so that, upon activation of the vibration device 14, the magnets are caused to vibrate and thereby produce a jet of high frequency oscillatory air via a piezo-electric-like mechanism. Advantageously, this configuration of the vibration device 14 (i.e., with magnets) does not require a motor for operation of the device, thereby decreasing the risk of component failure during critical periods of pulmonary ventilation.

The housing 34 can be made of one or a combination of hardened materials, such as plastic or metal. The housing 34 and the one or more vibrating elements 38 can define a chamber that is fluidly coupled to the at least one orifice 36. In one example, the housing 34 can include a first orifice 36' and an adjacent second orifice 36" that are fluidly coupled to the first and second prongs 24 and 28 of the Y-shaped adaptor 20 (respectively).

The signal generator component 40 can be disposed within the housing 34 and be configured or programmed to provide an electronic signal to the one or more vibrating elements 38. Application of an electronic signal to one of the vibrating elements 38 can cause the vibrating element to oscillate and thereby produce the jet of air. The signal generator component 40 can additionally or optionally include a controller (not shown). In some instances, the controller can include computer hardware and associated software programmed (e.g., pre-programmed) to deliver a desired number and frequency of electronic signals to the signal generator component 40. In other instances, a user (e.g., a physician) can manually operate the controller to selectively generate and deliver electronic signals to the signal generator component 40.

The vibration device 14 can further include a potentiometer 42. The potentiometer 42 can be in electrical communication with the signal generator component 40 and/or the controller. The potentiometer 42 can be used to selectively control the voltage input into the vibration device 14. Operation of the potentiometer 42 thus permits control of the frequency at which the vibrating element(s) 38 oscillate.

In another aspect, the system 10 (FIG. 1) can include a bifurcated cannula 16 that is fluidly coupled to the tubing array 12 (e.g., the third segment 30). The bifurcated cannula 16 can include first and second prongs 44 and 46 that are sized and dimensioned for placement proximate to (e.g., insertion into) first and second nostrils, respectively, of a neonate or infant. The first and second prongs 44 and 46 are independently movable with respect to one another. Thus, in some instances, the first and second prongs 44 and 46 can be connected to one another by a common section 48 or joint that allows the first prong to move freely relative to the second prong (and vice-versa). The independently movable prongs 44 and 46 are unlike conventional nasal cannulas, whose prongs are fixed and are not readily movable relative to one another. Advantageously, the bifurcated cannula 16 of the present disclosure provides a medical professional with a better way of delivering and weaning the cannula, which results in less damage to the nostrils. This is because, in use, one prong 44 or 46 of the bifurcated nasal cannula 16 can be disposed in one nostril while the other prong is absent from the other nostril. Consequently, the nostril without the prong 44 or 46 can do normal expiration and thereby give the nostril time to heal as the nostrils tend to become inflamed upon constant use of a nasal cannula.

It will be appreciated that the system 10 can include other components to assist in providing HFV to a neonate or infant in need thereof. For example, the system 10 can include a humidifier (not shown) that is fluidly coupled to the tubing array 12. Alternatively, the pressurized gas source 18 can include an integral humidifier that does not require a separate connection to the tubing array 12. As shown in FIG. 2, the vibration device 14 can also include a power source 39, which may be external or internal (e.g., a battery) to the vibration device.

Methods

Figure 3:
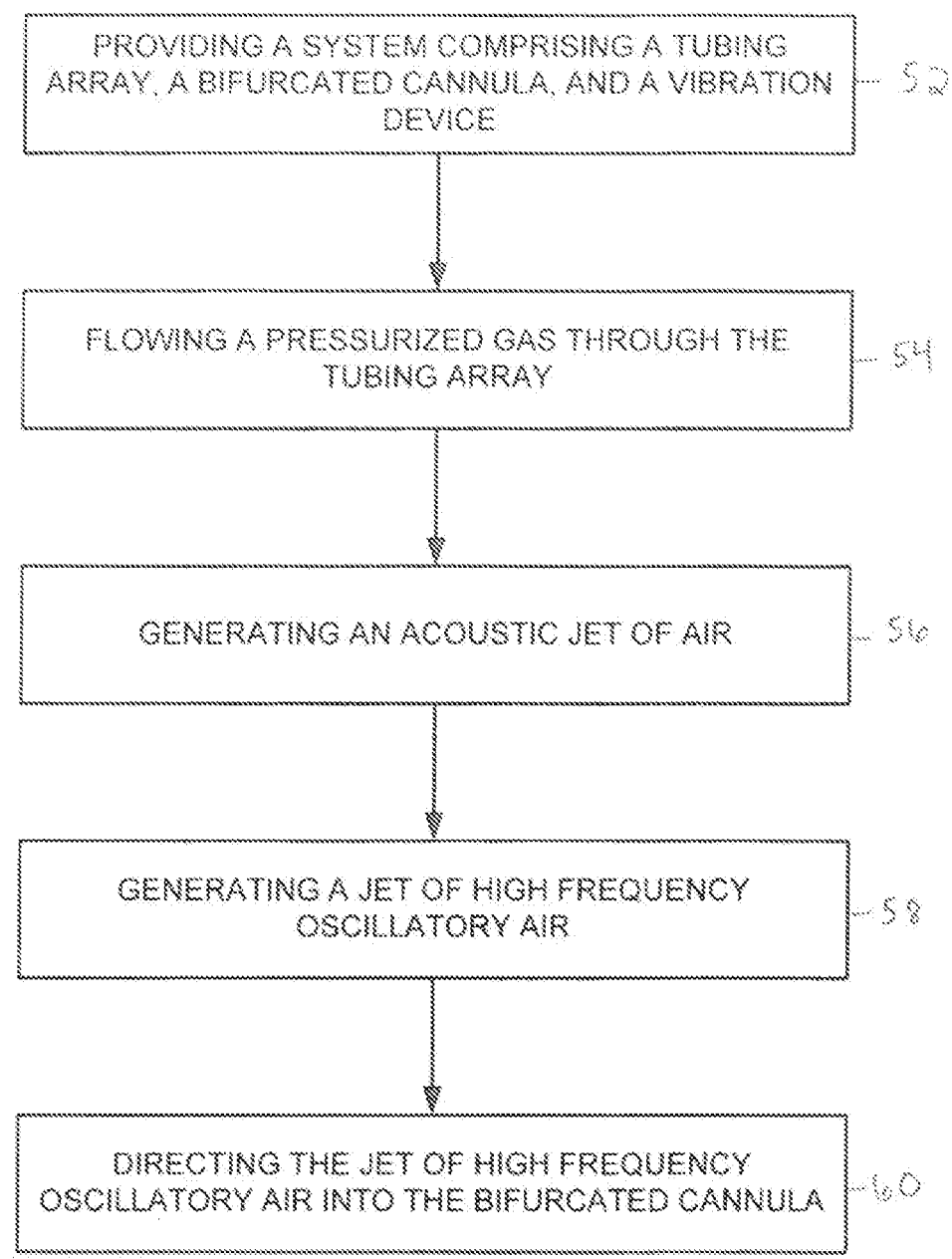
FIG. 3 is a process flow diagram illustrating a method for providing high frequency ventilation to a neonate or infant in need thereof according to another aspect of the present disclosure.

Another aspect of the present disclosure can include a method 50 (FIG. 3) for providing HFV to a neonate or infant in need thereof. In one example, the method 50 can be used to provide non-invasive, HFV to a pre-term neonate or pre-term infant in need thereof. As shown in FIG. 3, the method 50 can generally include the steps of: providing a system comprising a tubing array, a bifurcated cannula, and a vibration device (Step 52); flowing a pressurized gas through the tubing array (Step 54); generating a jet of air (Step 56); generating a jet of high frequency oscillatory air (Step 58); and directing the jet of high frequency oscillatory air into the bifurcated cannula (Step 60). Advantageously, the method 50 can be performed without intubating the neonate or infant.

At Step 52, a system 10 comprising a tubing array 12, a vibration device 14, and a bifurcated cannula 16 can be provided. The method 50 will be illustrated using the system 10 shown in FIGS. 1-2 and described above. It will be appreciated, however, that other configurations of the system 10 constructed in accordance with the scope and spirit of the present disclosure may also be provided at Step 52.

At Step 54, a pressurized gas can be flowed through the tubing array 12. The pressurized gas can be flowed from a pressurized gas source 18. In one example, the pressurized gas can comprise oxygen (or oxygen blended with air), and the pressurized gas source 18 can comprise a pressurized oxygen canister. A user can control the rate at which the pressurized gas is flowed through the tubing array 12. In one example, the pressurized gas can be flowed through the tubing array 12 at a rate of between about 0.5-10 L/min, about 1-9 L/min, about 1-5 L/min, about 2-8 L/min, about 3-7 L/min, about 4-6 L/min, about 8-10 L/min, less than about 1 L/min, about 1-2 L/min or less than about 2 L/min, depending upon the subject's need (e.g., based on the particular disease condition). The flow rate of the pressurized gas should be selected to avoid inadvertent administration of positive airway pressure. Where desired, the pressurized gas can be flowed through a humidifier (e.g., a bubble humidifier) at a desired rate.

At Step 56, a jet of air can be generated by the vibration device 14. The jet of air can be generated by delivering an electronic signal, which is generated by the signal generator component 40, to one or more vibrating elements 38 of the vibration device 14. The electronic signal(s) can be delivered at a frequency and for a duration sufficient to cause the vibrating element(s) 38 to oscillate and thereby generate the jet of air. Examples of such frequencies can include about 10-60 Hz, e.g., about 10-15 Hz, about 15-20 Hz, about 20-25 Hz, about 25-30 Hz, about 30-35 Hz, about 35-40 Hz, about 40-45 Hz, about 45-50 Hz, about 50-55 Hz, and about 55-60 Hz. In one example, the electronic signal(s) can be delivered at a frequency of about 55 Hz. The generated jet of air can exit the vibration device 14 via the Y-shaped adaptor 20 and flow through the tubing array 12 (e.g., the first segment 22)

until it is blended with the flow of pressurized gas (e.g., in the third segment 30) to generate a jet of high frequency oscillatory air (Step 58).

If it has not been done so already, the bifurcated cannula 16 can be positioned proximate to nose of the infant or neonate. For example, the first and second prongs 44 and 46 of the bifurcated cannula 16 can be at least partially disposed within the left and right nostrils of the infant or neonate (respectively). Once the bifurcated cannula 16 is appropriately positioned, the jet of high frequency oscillatory air can be directed into the bifurcated cannula (Step 60) so that the jet of high frequency oscillatory air flows through the first and second prongs 44 and 46 into the left and right nostrils (respectively) of the neonate or infant. The jet of high frequency oscillatory air can be flowed through the bifurcated cannula 16 at a desired flow rate and for a desired period of time. As discussed above, prolonged use of a nasal cannula can lead to unwanted irritation/inflammation of the nostrils. Thus, when desired, the bifurcated cannula 16 can be manipulated so that only the first prong 44 or only the second prong 46 remains in the left or right nostril (respectively) of the infant or neonate. Advantageously, this helps to minimize the amount of time the prongs 44 and 46 are disposed in the nostrils, which reduces irritation of the nostrils while still permitting delivery of the jet of high frequency oscillatory air to the infant or neonate.

Certain aspects of the present disclosure are illustrated by the following Examples. It is to be understood that the particular examples, materials, amounts, and procedures are to be interpreted broadly in accordance with the scope and spirit of the present disclosure as set forth herein.

Example 1

Figure 4:
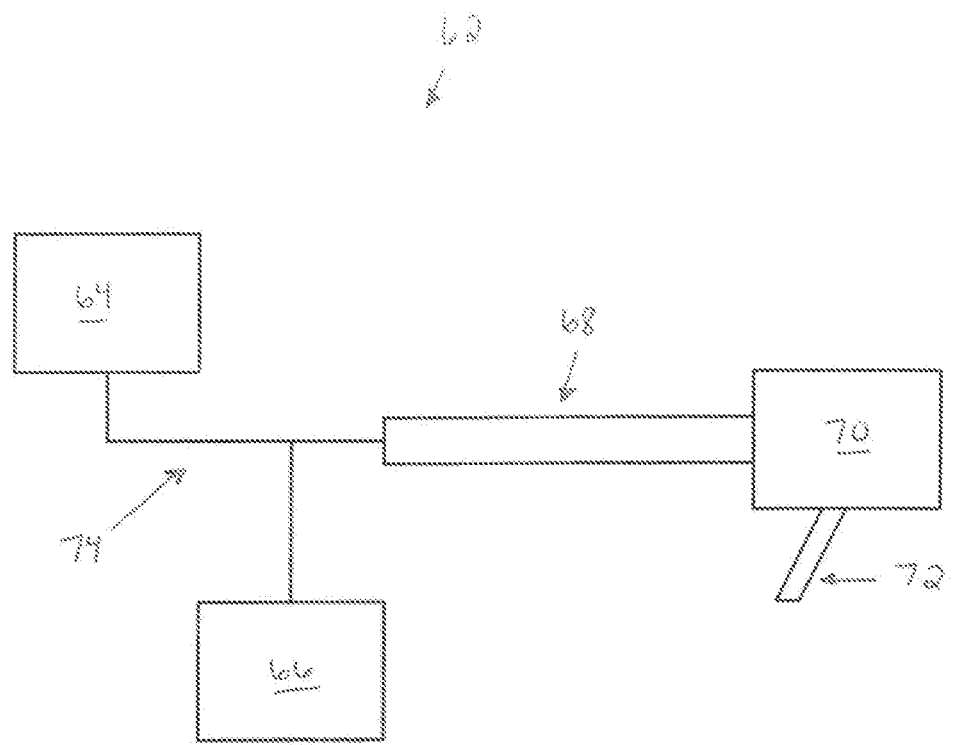
FIG. 4 is a schematic illustration of a high frequency nasal cannula circuit constructed in accordance with another aspect of the present disclosure.
Figure 5:
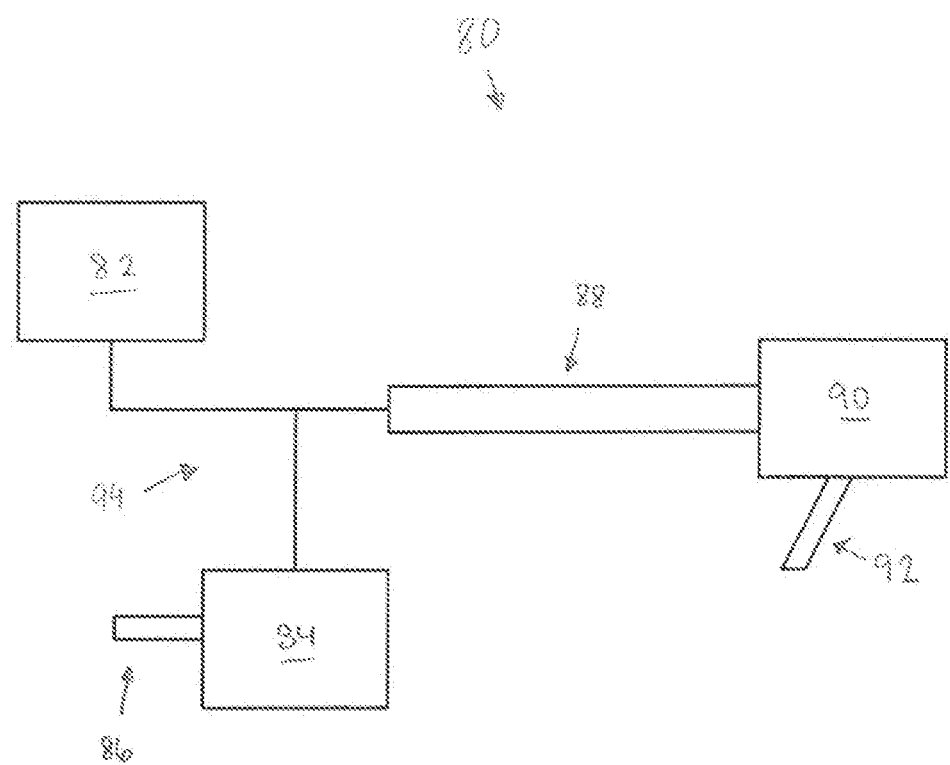
FIG. 5 is a schematic illustration showing a bubble CPAP circuit.

This Example describes an experiment designed to evaluate the efficacy of carbon dioxide removal using high a frequency nasal cannula (HIFI-NC) (FIG. 4) compared to bubble CPAP (B-CPAP) (FIG. 5). The HIFI-NC system 62 (FIG. 4) used in Example 1 and described below included (at least) a flow meter 64, a ventilator 66 (e.g., a Draeger Babylog ventilator), an endotracheal tube 68, and a bellows test lung 70, which includes a port 72. The flow meter 64 and the ventilator 66 were fluidly coupled to the endotracheal tube 68 via tubing 74. The B-CPAP system 80 (FIG. 5) used in Example 1 and described below included (at least) a flow meter 82, a bubble CPAP 84 with an exhaust port 86, an endotracheal tube 88, and a bellows test lung 90 having a port 92. The flow meter 82 and the bubble CPAP 84 were fluidly coupled to the endotracheal tube 68 via tubing 94.

Design/Methods

Time to eliminate $CO_2$ from a test lung, measured by end-tidal $CO_2$ ($ETCO_2$) has been shown to be a reproducible indicator of efficiency of ventilation. A 35 mL test lung attached to a pre-measured endotracheal tube was filled with 100% $CO_2$ and subjected to HIFI-NC (flow 5 L/min) or B-CPAP at 5cmH$_2$O for a period of 20 minutes. The test lung was then connected to a Draeger Babylog ventilator with a standard circuit, humidifier, flow sensor, and an in-line $ETCO_2$ monitor. The test lung was ventilated in A/C volume guarantee mode to ensure stable minute ventilation. PIP limit/PEEP 25/5 cmH$_2$O, IT 0.4 s, rate 60/min. and tidal volume 3.5 mL. The hypothesis was that, if HIFI-NC caused $CO_2$ to diffuse from the test lung more effectively than B-CPAP, there would be less $CO_2$ remaining after 20 minutes. The lower starting concentration of $CO_2$ would then make the $CO_2$ elimination time shorter at any given minute ventilation. $ETCO_2$ was continuously measured with a capnograph and exported to a spreadsheet. The time for $ETCO_2$ to fall to <8 mmHg (threshold of reliable detection by this instrument) was calculated for each experiment. Each experiment was repeated 3 times and the values were analyzed using paired t-test. p-values of <0.05 were considered significant.

Results

The recorded times for each experiment were highly reproducible. $CO_2$ elimination was significantly faster after 20 minutes of HIFI-NC vs. B-CPAP (see Table 1).

TABLE 1

| HIFI-NC $CO_2$ elimination time | B-CPAP $CO_2$ elimination time | P-value |
|---|---|---|
| 109 ± 15 seconds** | 140 ± 5 seconds | 0.01** |

In conclusion, HIFI-NC results in significantly faster $CO_2$ removal compared to B-CPAP.

Example 2

Figure 6:
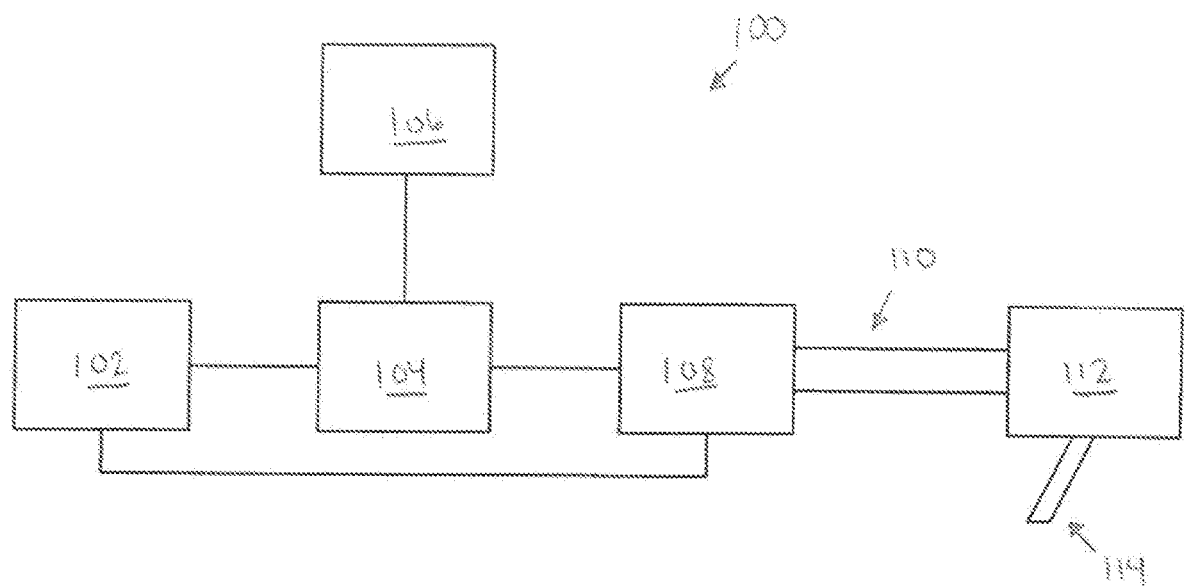
FIG. 6 is a schematic illustration showing a high flow nasal cannula circuit.

This Example describes an experiment showing that the efficacy of $CO_2$ removal is enhanced by HIFI-NC compared to regular high flow nasal cannula (HFNC) (FIG. 6) and ventilator generated CPAP (V-CPAP). The test system 100 (FIG. 6) used in Example 2 and described below included (at least) a ventilator 102 (e.g., a Babylog ventilator), a $CO_2$ sensor 104, a capnograph 106 in electrical communication with the $CO_2$ sensor, a flow sensor 108 in electrical communication with the ventilator, an endotracheal tube 110, and a bellows test lung 112 having a port 114. The ventilator 102 was connected to other components via tubing 116.

Design/Methods

A 35 mL test lung attached to a pre-measured endotracheal tube was filled with 100% $CO_2$ and subjected to HFNC (5 L/min), HIFI-NC (flow 5 L/min) or V-CPAP at 5cmH$_2$O for a period of 20 minutes, after which the lung was connected to a Babylog ventilator, standard circuit, humidifier, flow sensor, and an in-line $ETCO_2$ monitor. The test lung was ventilated in A/C volume guarantee mode to ensure stable minute ventilation (MV). PIP limit/PEEP 25/5 cmH$_2$O, IT 0.4 s, rate 60/min. and tidal volume 3.5 mL. The hypothesis was that, if HIFI-NC caused $CO_2$ to diffuse from the test lung faster, there would be less $CO_2$ remaining after 20 minutes. The lower starting concentration of $CO_2$ would then make the $CO_2$ elimination time shorter at a given MV. $ETCO_2$ was continuously measured with a capnograph and exported to a spreadsheet. The time for $ETCO_2$ to fall to <8 mmHg (threshold of reliable detection by this instrument) was calculated for each run. Each experiment was repeated 3 times and the values were analyzed using ANOVA. p-values of <0.05 were considered significant.

Results $CO_2$ elimination was significantly faster with HIFI-NC vs. HFNC and V-CPAP (see Table 2).

TABLE 2

| HIFI-NC $CO_2$ elimination time | HFNC $CO_2$ elimination time | V-CPAP $CO_2$ elimination time | P-value |
|---|---|---|---|
| 109 ± 15 seconds** | 179 ± 7 seconds | 175 ± 11 seconds | <0.05** |

In conclusion, oscillations provided by HIFI-NC improve the efficacy of $CO_2$ removal compared to V-CPAP or HFNC alone.

From the above description of the present disclosure, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

The following is claimed:

1. A system for providing high frequency ventilation to a neonate or an infant in need thereof, the system comprising:
    a tubing array adapted to receive a flow of pressurized gas therethrough;
    a vibration device fluidly coupled to the tubing array, the vibration device including at least two magnets that are configured to vibrate and/or oscillate, the vibration and/or oscillation of the at least two magnets directly producing a jet of air that is applied to the flow of the pressurized gas; and
    a bifurcated cannula fluidly coupled to the tubing array and having independently movable first and second prongs that are sized and dimensioned for insertion into first and second nostrils, respectively, of the neonate or the infant.

2. The system of claim 1, wherein the vibration device further comprises:
    a housing having at least one orifice;
    the at least two magnets being located within the housing, the at least two magnets and the housing defining a chamber that is fluidly coupled to the at least one orifice; and
    a signal generator electrically coupled to the at least two magnets and configured to provide an electronic signal to the at least two magnets to cause the at least two magnets to oscillate within the housing;
    wherein oscillation of the at least two magnets produces the jet of air.

3. The system of claim 2, wherein the at least one orifice comprises a first orifice and a second orifice, wherein the first and second orifices being configured to receive a Y-shaped adaptor.

4. The system of claim 2, wherein the signal generator is configured to deliver the electronic signal signal to the at least two magnets sufficient to cause the at least two magnets to oscillate at a frequency in the range of 50 to 60 Hz.

5. The system of claim 1, wherein the first prong and/or second prong of the bifurcated nasal cannula is/are configured to be positioned proximate to the first and/or second nostril(s) of the neonate or the infant, respectively.

6. The system of claim 1, wherein the tubing array further comprises:
    a Y-shaped adaptor;
    a first segment of tubing that fluidly couples the at least one orifice of the vibration device to a first prong of the Y-shaped adaptor;
    a second segment of tubing that fluidly couples the source of pressurized gas to a second prong of the Y-shaped adaptor; and
    a third segment of tubing that fluidly couples the bifurcated nasal cannula to a third prong of the Y-shaped adaptor.

7. The system of claim 1, wherein the neonate or infant is a pre-term neonate or infant.

8. A non-invasive method for providing high frequency ventilation to a neonate or infant in need thereof, the method comprising the steps of:
    generating a jet of high frequency oscillatory air, wherein the jet of high frequency oscillatory air is directly generated by oscillatory motion of at least two magnets within a housing of the vibration device, the vibration device being fluidly coupled to a tubing array adapted to receive a flow of pressurized gas therethrough; and
    directing the jet of high frequency oscillatory air through a first prong and/or a second prong of a bifurcated cannula, which is positioned proximate to the first and/or second nostril(s) of the neonate or the infant, respectively.

9. The method of claim 8, wherein the jet of high frequency oscillatory air is directed through only the first prong or only the second prong of the bifurcated cannula.

10. The method of claim 8, wherein the generating step further comprises the steps of:
    delivering, by an electric signal generator comprising the vibration device, an electronic signal to the at least two magnets to generate the jet of air; and
    combining the jet of air with the flow of pressurized gas to create the jet of high frequency oscillatory air.

11. The method of claim 10, wherein the signal generator is configured to deliver the electronic signal to the least two magnets sufficient to cause the vibrating element(s) to oscillate at a frequency of about 55 Hz.

12. The method of claim 8, wherein the housing comprises a first orifice and second orifice, the first and second orifices being configured to receive a Y-shaped adaptor.

13. The method of claim 8, wherein the tubing array further comprises:
    a Y-shaped adaptor;
    a first segment of tubing that fluidly couples the at least one orifice of the vibration device to a first prong of the Y-shaped adaptor;
    a second segment of tubing that fluidly couples the source of pressurized gas to a second prong of the Y-shaped adaptor; and
    a third segment of tubing that fluidly couples the bifurcated nasal cannula to a third prong of the Y-shaped adaptor.

14. The method of claim 8, wherein the neonate or infant is a pre-term neonate or infant.

15. The method of claim 8, being performed without intubating the neonate or infant.

\* \* \* \* \*